US008580766B2

(12) United States Patent
Marcum

(10) Patent No.: US 8,580,766 B2
(45) Date of Patent: *Nov. 12, 2013

(54) GLYCOSAMINOGLYCAN COMPOSITION AND METHOD FOR TREATMENT AND PREVENTION OF INTERSTITIAL CYSTITIS

(75) Inventor: Frank D. Marcum, Versailles, KY (US)

(73) Assignee: ArthroDynamic Technologies, Animal Health Division, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/363,265

(22) Filed: Jan. 30, 2009

(65) Prior Publication Data

US 2009/0137525 A1    May 28, 2009

Related U.S. Application Data

(63) Continuation of application No. 11/105,163, filed on Apr. 13, 2005, now Pat. No. 7,504,387, which is a continuation-in-part of application No. 11/015,137, filed on Dec. 17, 2004, now Pat. No. 7,485,629, and a continuation-in-part of application No. 10/686,918, filed on Oct. 16, 2003, now Pat. No. 6,979,679.

(60) Provisional application No. 60/419,009, filed on Oct. 16, 2002, provisional application No. 60/487,861, filed on Jul. 16, 2003.

(51) Int. Cl.
*A61K 31/70* (2006.01)

(52) U.S. Cl.
USPC ............................................... 514/54; 514/62

(58) Field of Classification Search
None
See application file for complete search history.

(56) References Cited

U.S. PATENT DOCUMENTS

| | | | |
|---|---|---|---|
| 3,697,652 A | 10/1972 | Rovati et al. |
| 4,801,619 A | 1/1989 | Lindblad |
| 4,808,576 A | 2/1989 | Schultz et al. |
| 5,180,715 A | 1/1993 | Parsons |
| 5,364,845 A | 11/1994 | Henderson |
| 5,587,363 A | 12/1996 | Henderson |
| 5,591,724 A | 1/1997 | Morales et al. |
| 5,843,919 A | 12/1998 | Burger |
| 5,880,108 A | 3/1999 | Morales et al. |
| 5,888,986 A | 3/1999 | Morales et al. |
| 5,994,357 A | 11/1999 | Theoharides |
| 6,083,933 A | 7/2000 | Hahn |
| 6,255,295 B1 | 7/2001 | Henderson et al. |
| 6,432,929 B1 | 8/2002 | Stone |
| 6,506,785 B2 | 1/2003 | Evans |
| 6,608,041 B2 | 8/2003 | Hammerly |
| 6,635,625 B2 | 10/2003 | Theoharides |
| 6,906,044 B2 | 6/2005 | Hermida Ochoa |
| 6,924,273 B2 | 8/2005 | Pierce |
| 6,949,525 B2 | 9/2005 | Hermida |
| 6,979,679 B2 | 12/2005 | Marcum |
| 6,984,667 B2 | 1/2006 | Theoharides |
| 2002/0068718 A1 | 6/2002 | Pierce |

FOREIGN PATENT DOCUMENTS

GB    2317109 A    3/1998

OTHER PUBLICATIONS

Campo et al, "Administration of Hyaluronic Acid and Chondroitin-4-Sulfate Limits Endogenous Antioxidant Depletion and Reducess Cell Damage in Experimental Acute Pancreatis", Pancreas, vol. 28, No. 2, Mar. 2004, pp. e45-e53.*
Bassleer et al., 1998, "Stimulation of Proteglycan Production by Glucosamine Sulfate in Chondrocytes Isolated from Human Osteoarthritic Articular Cartilage in Vitro," Osteoarthritis and Cartilage, vol. 6, pp. 427-434.
Bucci et al., 1994, "Glucosamine Salts and Chondroitin Sulfates," Townsend Letter for Doctors, pp. 52-54.
Capps et al., 1966, "Hexosamine Metabolism," Biochimica et Biophysica ACTA, 127:194-204.
Coleman et al., 1999, "Characterization of the Effect of High Molecular Weight Hyaluronan on Trans-Synovial Flow in Rabbit Knees," Journal of Physiology, 514.1, pp. 265-282.
Coleman et al., 1997, "Hyaluronan Secretion into the Synovial Cavity of Rabbit Knees and Comparison with Albumin Turnover," Journal of Physiology, 503.3, pp. 645-656.
Coleman et al., 2000, "Role of Hyaluronan Chain Length in Buffering Interstitial Flow Across Synovium in Rabbits," Journal of Physiology, 526.2, pp. 425-434.
Day et al., 2002, "Hyaluronan-Binding Proteins: Tying up the Giant," The Journal of Biological Chemistry, vol. 277, No. 7, pp. 4585-4588.
Dorna et al., "Effects of Oral and Intramuscular Use of Chondroitin Sulfate in Induced Equine Aseptic Arthritis."
Hinderlich et al., 2000, "Molecular Cloning and Characterization of Murine and Human N-acetylglucosamine Kinase," Eur. J. biochem., 267:3301-3308.
Johnson et al., 2001, "Chondroitin Sulfate," Continuing Education Module from the New Hope Institute of Retailing.

(Continued)

*Primary Examiner* — Elli Peselev
(74) *Attorney, Agent, or Firm* — Sutherland Asbill & Brennan LLP

(57) ABSTRACT

The invention provides compositions and methods useful for the treatment and/or prevention of interstitial cystitis and/or a related urinary tract condition in man or in animals. Specifically, provided are compositions specially formulated for direct instillation into the bladder and/or parenteral use in the treatment and/or prevention of interstitial cystitis. Compositions adapted for direct instillation into the bladder and/or for systemic administration are provided comprised of therapeutic amounts of: chondroitin sulfate in combination with hyaluronan (hyaluronic acid) are provided. Compositions adapted for direct instillation into the bladder and/or for systemic administration are also provided comprised of therapeutic amounts of: chondroitin sulfate, hyaluronan (hyaluronic acid) and N-acetyl D-glucosamine.

15 Claims, No Drawings

(56) References Cited

OTHER PUBLICATIONS

McIlwraith, "Traumatic Joint Injuries and Disease," http://www.equineortho.colostate.edu/questions/tjd.htm.

Murray M.: "Glucosamine sulfate: effective osteoarthritis treatment." Amer. J. Nat. Med. Sep. 10-14, 1994.

Sabaratnam et al., 2002, "Interactive Effect of Chondroitin Sulphate C and Hyaluronan on Fluid Movement Across Rabbit Synovium," Journal of Physiology, 540.1, pp. 271-284.

Schiavinato et al., 2002, "Comparison of the Effects of Intra-Articular Injections of Hyaluronan and Its Chemically Cross-Linked Derivative (Hylan G-F20) in Normal Rabbit Knee Joints," Clinical and Experimental Rheumatology, 20:445-454.

Shikhman et al., 2001, "N-Acetylglucosamine Prevents IL-1beta-Mediated Activation of Human Chondrocytes," The American Association of Immunologists.

Tersariol et al., 2002, "Proteinase Activity Regulation by Glycosaminoglycans," Brazilian Journal of Medical and Biological Research, 335:135-144.

Todhunter et al., 1993, "Effects of Exercise and Polysulfated Glycosaminoglycan on Repair of Articular Cartilage Defects in the Equine Carpus," Journal of Orthopaedic Research, 11:782-795.

Heart et al., 2002, "Glucose Transport by Osmotic Shock and Vanadate is Impaired by Glucosamine," Biochem Biophys Res Commun; 292:308-11.

de Mattei et al., 2002, "High Doses of Glucosamine-HC1 have Detrimental Effects on Bovine Articular Cartilage Explants Cultured in vitro," Osteoarthritis-Cartilage.; 10(10):816-25.

Breborowicz et al., 1998, "The effect of N-acetylglucosamine as a substrate for in vitro synthesis of glycosaminoglycans by human peritoneal mesothelial cells and fibroblasts," Adv Pent Dial; 14:31-5.

\* cited by examiner

GLYCOSAMINOGLYCAN COMPOSITION AND METHOD FOR TREATMENT AND PREVENTION OF INTERSTITIAL CYSTITIS

CROSS REFERENCES TO RELATED APPLICATIONS

This patent application is a continuation of U.S. application Ser. No. 11/105,163 filed Apr. 13, 2005, now U.S. Pat. No. 7,504,387, which is a continuation-in-part of U.S. application Ser. Nos. 11/015,137 filed on Dec. 17, 2004, now U.S. Pat. No. 7,485,629, which is a continuation-in-part of application Ser. No. 10/686,918 filed on Oct. 16, 2003, now U.S. Pat. No. 6,979,679 which claims priority to U.S. Provisional Application Nos. 60/419,009 and 60/487,861 filed Oct. 16, 2002 and Jul. 16, 2003, respectively.

FIELD OF INVENTION

The present invention is generally directed to compositions comprised of glycosaminoglycans and/or glycosaminoglycan precursors that are useful for the treatment and/or prevention of disease in man and in animals. Specifically, the invention relates to compositions comprised of glycosaminoglycans and/or glycosaminoglycan precursors specially formulated for use in the treatment and/or prevention interstitial cystitis and related urinary tract conditions.

BACKGROUND OF THE INVENTION

Interstitial cystitis (IC) is a chronic inflammatory condition of the bladder of unknown etiology. Interstitial cystitis can affect people of any age, race or sex, however, IC is most commonly found in women. Recent epidemiological data suggest that there may be greater than 700,000 cases of IC in the U.S. alone.

Interstitial cystitis is characterized by irritative voiding symptoms, symptoms of urinary urgency, frequency, dysuria, nocturia, and suprapubic or pelvic pain related to and relieved by voiding. "Common" cystitis, also known as a urinary tract infection, is caused by bacteria and is usually successfully treated with antibiotics. Unlike common cystitis, IC is generally believed not to be caused by bacteria and does not respond to conventional antibiotic therapy. It is important to note that IC is not a psychosomatic disorder nor is it believed to be caused by stress.

Symptoms or clinical signs of interstitial cystitis (IC) can include: 1) frequency of urination (whether day or night) the frequency of urination can be up to 60 times a day in severe cases. In early or very mild cases of IC, frequency of urination is sometimes the only symptom; 2) urgency of urination, i.e., the sensation of having to urinate immediately, which may also be accompanied by pain, pressure or spasms; 3) pain which can be in the lower abdominal, urethral or vaginal area. Pain is also frequently associated with sexual intercourse. Men with IC may experience testicular, scrotal and/or perineal pain, and painful ejaculation.; and 4) other disorders, e.g., some patients also report muscle and joint pain, migraines, allergic reactions, gastrointestinal problems and skin problems as well as the more common symptoms of IC described above. It appears that IC has an as yet unexplained association with certain other chronic diseases and pain syndromes such as vulvar vestibulitis, fibromyalgia and irritable bowel syndrome. Many IC patients, however, have only bladder symptoms.

Symptoms of IC are usually present for many years before diagnosis and they usually peak and stabilize within a few years of diagnosis. Progression of the disease often leads to social and emotional crippling. The pain and frequency may interfere with an individual's ability to work and to socialize, and the nocturia may lead to chronic loss of sleep.

The prevalence in some IC patients of headaches, gastrointestinal and skin problems may tend to suggest that interstitial cystitis may represent the end organ (bladder) response of a systemic condition affected by many heterogeneous stimuli triggering a common denominator, e.g., the mast cell. However, the pathology and pathogenesis of IC have not been clearly elucidated. Proposed theories include infection, vascular obstruction, autoimmunity, inflammatory, neurogenic and endocrine causes.

The role of the mast cell in the bladder wall and the bladder surface protective glycosaminoglycan (GAG) layer are areas of research interest. Research indicates that mast cells in the bladder may be activated in IC without necessarily increasing the total numbers of cells. Histamine and other mediator release in the bladder wall of IC patients may be a pathogenetic mechanism for the causation of the disease. It is uncertain whether the mast cell is a consequence of IC or a pathogenetic factor in its causation.

Most IC patients have difficulty in obtaining a definitive diagnosis of IC. To make a proper diagnosis of IC, a urologist will typically: 1) obtain a urine culture to determine if there is a bacterial infection present; 2) rule out other diseases and/or conditions that have symptoms resembling IC. These diseases may include bladder cancer, kidney problems, tuberculosis, vaginal infections, sexually transmitted diseases, endometriosis, radiation cystitis and neurological disorders; and 3) perform a cystoscopy with hydrodistention under general anesthesia if no infection is present and no other disorder is discovered. If distention under anesthesia is not performed, the diagnosis of IC may be missed. Cystoscopy during a routine office visit may not reveal the characteristic abnormalities of IC and can be painful for those who have IC. Therefore, it is necessary to distend the bladder under general or regional anesthesia in order to see the pinpoint hemorrhages on the bladder wall that are essentially pathopneumonic for this disease. In some cases, a biopsy of the bladder wall may be necessary to rule out other diseases such as bladder cancer and to assist in the diagnosis of IC because IC is not usually associated with bladder cancer.

Currently, there is no cure for IC, nor is there an effective treatment which works for everyone. Prior to the present invention treatments have been aimed at a variety of therapeutic regimens including, oral medications, bladder instillations, diet regulation, nerve stimulation, and/or surgery. ELMIRON® (pentosan polysulfate sodium) received FDA approval in 1996 and is the only oral medication approved specifically for use in IC. It is believed to work by repairing a thin or damaged bladder lining (See e.g., U.S. Pat. No. 5,180, 715, to Parsons which discloses a method of treating bladder infections, IC and tumors in mammals comprising the oral administration of sodium pentosanpolysulfate at high dosages on the order of 200 mg. per day or more). Also disclosed is a method comprising irrigation of the internal bladder and associated surfaces with an irrigating solution containing an effective amount of sodium pentosanpolysulfate.

Other oral medications that have been used in the treatment of IC include tricyclic antidepressants such as Elavil® (amitriptyline) which has been shown to help with both the pain and frequency of IC. In IC, these medications are used for their anti-pain properties, not as a treatment for depression. Other oral medications include anti-inflammatory agents, antispasmodics, bladder analgesics, such as Urimax®, antihistamines, and muscle relaxants. For example, U.S. Pat. No.

5,994,357, to Theoharides discloses a method of treating patients suffering from IC comprising the administration of an inhibitor of neuroliormonal activation of mast cell secretion e.g., a histamine-I receptor antagonist consisting of azatadine, azelastine, cetirizine, hydroxyzine and ketotifen, by oral, parenteral, transmucosal, and transdermal routes of administration.

Another method of treatment of IC comprises a regimen of bladder instillations or bladder distention with various therapeutic agents. In bladder distention, the bladder is stretched by filling it with water under general anesthesia. This is part of the diagnostic procedure for IC, and may be therapeutic as well. DMSO (dimethyl sulfoxide) is a medication that is sometimes instilled directly into the bladder. DMSO is believed to work as an anti-inflammatory agent and therefore reduces pain. DMSO can be mixed with steroids, heparin, and/or local anesthetics to form a bladder "cocktail."

BCG (bacillus Calmette-Guerinii) mycobacterium bovis derived immune stimulant is an instillation agent that is an experimental treatment currently in the clinical phrase and is not yet approved for IC by the FDA. It is, however, approved for the treatment of bladder cancer and it appears to work by boosting the immune system. CYSTISTAT® (hyaluronic acid) is another instillation product that is in clinical trials and is not yet approved for use in IC in the United States. It is thought to work by replacing the defective lining of the bladder with a coating of hyaluronic acid. For example U.S. Pat. Nos. 5,591,724; 5,880,108; and 5,888,986 to Morales et al. disclose methods of treating IC comprising contacting the internal bladder and associated structures in a mammal having interstitial cystitis with a solution containing hyaluronic acid.

Other infusion therapies include, e.g., U.S. Pat. No. 6,083,933 to Hahn which discloses a method of treatment of cystitis of the bladder and urinary tract, particularly interstitial cystitis, using effective unit doses of chondroitin sulfate. Cystitis patients are screened for their response to a given cystitis treatment using a method in which patients are first challenged with an irritant and then treated with a selected cystitis therapeutic such as chodroitin sulfate. Likewise, Clorpactin WCS-90 (oxychlorosene sodium), has been tried as an instillation agent, however, its use can be very painful and requires general anesthesia. Silver Nitrate is also used infrequently and is now considered an outdated therapy.

Other therapeutic measures include diet. The elimination of certain foods (acidic, spicy) may decrease the severity of IC symptoms. Also, smoking, drinking coffee or tea, and alcoholic beverages may aggravate IC. Prelief, an over-the-counter dietary supplement, has also been tired to help IC patients better tolerate acid foods and beverages.

Self-help techniques may improve the quality of life and reduce the incidence and severity of flare-ups of IC. These include changes in diet, stress reduction, visualization, biofeedback, bladder retraining and exercise, among others. Electronic nerve stimulators, e.g., Transcutaneous Electrical Nerve Stimulation (TENS) have also been tried as a therapeutic to combat IC. This device, which is worn externally, has been shown to relieve bladder pain in some people. Sacral Nerve Stimulation Implants are surgically implanted devices that are approved for use in treating urinary incontinence, urgency and frequency. They are not yet FDA-approved for treating IC pain, but are currently undergoing testing for this purpose.

For a small minority of patients whose symptoms are severe and who do not respond to other IC treatments, bladder surgery may be considered. However in some cases, IC symptoms may not improve. Several types of surgery have been used to treat IC, including cystectomy and urinary diversion. Laser surgery has been reserved solely for the Hunner's ulcer form of IC.

Although the above-mentioned therapeutic measures have met with varying degrees of success, there still remains a need in the art for a simple, safe and effective treatment and/or preventative for IC and its sequella which will relieve and/or prevent the devastating effects of the complicated and poorly understood IC disease process.

More importantly, prior to the present invention there has not been a single effective composition specifically formulated for use as a medical device for direct bladder installation that combines an optimal combination of active agents which can be used for instillation therapy in the treatment of IC. In particular, there exists a need in the art for a composition formulated for direct bladder installation use that uniquely combines synergistically active agents for use in a method of treatment of IC or related urinary tract conditions in man and in animals.

Likewise, prior to the present invention there has not been a single effective composition specifically formulated for parenteral (e.g., intravenous or intramuscular) use which combines an optimal combination of active agents which can be used for intra-parenteral treatment of IC. In particular, there exists a need in the art for a composition formulated for parenteral or other systemic use which combines synergistically active agents to treat and/or prevent IC and/or related urinary tract conditions in man and in animals.

SUMMARY OF THE INVENTION

A primary object of the present invention is to provide an improved composition and related method for treatment and/or prevention of interstitial cystitis, by providing a composition adapted for direct bladder instillation which can be used as a treatment and/or preventative to alleviate or lessen at least one symptom of interstitial cystitis (IC) or a related urinary tract condition in man or in animals.

In one embodiment for the methods of treatment and/or prevention of IC, the invention provides a composition adapted for use as a medical device that is suitable for direct intra bladder instillation that is comprised of therapeutic amounts of: chondroitin sulfate in combination with hyaluronan (hyaluronic acid). In one embodiment, for example, the therapeutic amount of chondroitin sulfate can be from about 0.5 to 1.5 grams of chondroitin sufate and the therapeutic amount of hyaluronic acid can be from about 10 mg to about 50 mg per unit dose of the composition. The chondroitin sulfate may preferably comprise a mixture of CS4 and CS6 chondroitin sulfate wherein the mixture the mixture can be from about 70% CS4 to about 30% CS4 and from about 30% CS6 to about 70% CS6. In addition, in a presently preferred embodiment of the invention, the hyaluronic acid (HA) may be a Streptococcus derived (synthetically produced) HA having a molecular weight of at least about 250,000 KD and optionally may be at least about 500,000 KD. In still another embodiment of the invention, the molecular weight of the HA of the invention is at least about 750,000 KD and optionally may be at greater than about 1,000,000 KD.

The compositions of one embodiment of the invention provide a chondroitin sulfate, (as CS4 and/or CS6) adapted for direct bladder instillation that is in a required combination with hyaluronic acid. The chondroitin sulfate of the compositions provided herein is preferably in solution or suspension with hyaluronic acid. In another embodiment of the methods for the treatment and/or prevention of IC, the invention provides a composition adapted for parenteral and/or other systemic use that is comprised of therapeutic amounts of: chondroitin sulfate in combination with hyaluronan (hyaluronic acid), which may optionally be in solution and/or suspension with N-acetyl D-glucosamine.

In yet another embodiment for the prevention and/or treatment of IC, the invention provides a composition adapted systemic or parenteral administration comprised of therapeutic amounts of: chondroitin sulfate in a required combination with hyaluronan (hyaluronic acid). Systemic administrations can include but are not limited to intramuscular, intravenous or subcutaneous injection.

In certain embodiments of the invention, the compositions may further optionally include N-acetyl D-glucosamine. In one embodiment, the hyaluronic acid and chondroitin sulfate of the composition is in a solution of N-acetyl D-glucosamine. The N-acetyl D-glucosamine provided in the compositions of the invention may provide a bridge to cross link with HA at its binding site as well as acting as a solution carrying precursor of the HA/CS link molecule versican/aggregan for the purpose of providing a supramolecular complex with link proteins to form a strongly hydrated space filling gel of poly-anionic glycosaminoglycan chains covalently attached to the core and contributing to the strength of the bladder GAG layer.

DETAILED DESCRIPTION OF THE INVENTION

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to novel compositions and methods for treatment and/or prevention of interstitial cystitis and/or related urinary tract conditions. In particular, the present invention provides specific teachings related to an improved composition and related method for treatment and/or prevention of interstitial cystitis, by providing a composition adapted for direct bladder instillation whici can be used as a treatment and/or preventative to alleviate or lessen at least one symptom of interstitial cystitis (IC) or a related urinary tract condition in man or in animals. In addition, the present invention provides compositions and surprisingly novel methods for the parenteral (systemic) and/or oral treatment and/or prevention of interstitial cystitis. While oral administration of the compositions of the invention is not the presently preferred embodiment for the methods of the invention, it is contemplated that the compositions set forth herein can be utilized in a formulation adapted for oral administration for the treatment and/or prevention of interstitial cystitis. The examples set forth herein are in no way intended to limit the scope of the invention. Those of skill in the art will realize that, given the teachings provided herein, many variations of the methods are possible that will fall within the scope of the of the invention.

In one embodiment, the invention provides a composition adapted for direct instillation into the bladder, that is useful for the treatment and/or prevention of interstitial cystitis, the composition comprising therapeutic amounts of: chondroitin sulfate; hyaluronan (hyaluronic acid) and may optionally include N-acetyl D-glucosamine.

While not wishing to be bound to any particular theory, it is believed that the glucosaminoglycans present in the compositions provided herein help to contribute to the return of homeostasis of the bladder wall through the supramolecular complex of strongly hydrated space filling gel of poly-anionic GAG chains covalently attached to the core of the bladder GAG layer and providing physical strength to the tissue. In addition to that effect, the incorporation of chondroitin sulfate into the compositions provided herein helps slow down the inflammatory process, by liganding to the CD44 and TSG-6 ligand receptor sites acting directly on the enzymes and inflammatory mediators that are released when inflammation is present.

The sodium hyaluronate (hyaluronan or hyaluronic acid) provided by the compositions serves to cover the surface or transitional epithelial lining of the bladder (bladder wall) with a thin coating of the above supra molecule. Hyaluronan also directly acts as an inhibitor of inflammatory mediators by its direct effect on CD44 receptor ligands which mediates the migration of lymphocytes during inflammation.

When present in the compositions of the invention, the N-acetyl D-glucosamine acts to link the supramolecular complex in solution as well as acting as a precursor to form new chains by the existing GAG layer.

The compositions of the invention provide a unique mixture comprised of the naturally occurring glucosaminoglycans: chondroitin sulfates CS4 and CS6, and hyaluronan (hyaluronic acid). Glucosaminoglycans are polysacchrides which occur widely in the animal kingdom. Glucosaminoglycans that are present in the tissues of vertebrate animals have mainly a linear structure which is repetition of a disaccharide units composed of two monosaccharides. Five kinds of glucosaminoglycans are found in the tissues and fluids of vertebrates: chondroitin sulfates, keratin sulfates, dermatin sulfates, heparin sulfates; hyaluronic acid and heparin.

Chondroitin sulfates are one critical component of certain embodiments of the compositions of the invention. In general, chondroitin sulfates are widely found in the connective tissues of animals in two forms of repeating disaccharides of D-glucouronic acid and N-acetyl galactosamine: CS4 sulfate where N-acetyl galactosamine holds an ester sulfate in its CS4 position or CS6 sulfate where the ester sulfate is in the CS6 position. Both CS4 and CS6 chondroitin sulfate function in the aiticular matrix as a major constituent. Chondroitin sulfates contribute to keep the intracellular matrix's normal characteristics through the binding with HA to form the core of the supramolecular complex, as well as slowing down the inflammatory process acting directly on the enzymes inhibiting the compliment cascade and by exhibiting anti-prostoglandin activity.

In particular, chondroitin sulfate is a long hydrophilic chain of repeating sugars. This glycosaminoglycan binds to proteoglycan molecules aiding in the attachment of the supramolecular complex to the core protein as well as the bladder GAG tissue layer. Chondroitin in its sulfate form includes galactosamine, a primary substrate of hylauronan and a disaccharide pathway for proteoglycan synthesis secondary to the hexosamine pathways utilized for glycosaminoglycan production. Chondroitin stimulates the production of proteoglycans, glycosaminoglycans, and collagen, which are the building blocks of a healthy bladder GAG layer. Chondroitin sulfate also inhibits the secretion of degenerative enzymes by the liganding CS4 on the TSG-6 receptor responsible for inflammation. Chondroitin Sulfates are non-toxic and work synergistically with glucosamine to hydrate and repair the GAG layer of the bladder wall. Chondroitin sulfate also works synergistically with hyaluronic acid to form the supramolecular matrix core to increase viscosity of the compositions of the invention and thereby increase the coating/protective properties of compositions as they bind to the GAG layer of the bladder wall. (see e.g., Hyaluroninin Synovial Joints: Molecular Seiving, Concentration Polarization & Secretion Regulation in vivo" Coleman et al., Matrix Biology Institute 2004).

Another critical component of certain embodiments of the compositions of the invention, sodium hyaluronate, is a natural constituent of connective tissues and synovial fluid composed of repeating disaccharide units each consisting of D-glucoronic acid and N-acetyl D-giucosamine. Hyaluronan aids in providing nourishment and waste removal from the intracellular matrix. When combined with chondroitin sulfate, the exogenous hyaluronin present in the compositions of the invention acts synergistically with the chondroitin sulfate to aid in the treatment and/or prevention of interstitial cystitis.

Therefore, one embodiment of the invention provides a composition adapted for direct intra-bladder instillation and/or other parenteral injection that is useful for the treatment and/or prevention of interstitial cystitis, by providing a composition which can be used as a treatment and/or preventative to alleviate or lessen at least one symptom of interstitial cystitis (IC) or a related urinary tract condition in man or in animals, the composition comprising therapeutic amounts of: chondroitin sulfate and hyaluronan in the substantial absence of other naturally occurring or synthetic glycosaminoglycans, e.g, other as set forth, eg., in U.S. Pat. No. 5,180,175 to Parsons etc.

In general, the compositions of certain embodiments of the invention may optionally include N-acetyl D-glucosamine. N-acetyl D-glucosamine also possesses the ability to provide a bridge to cross link with HA at its binding site as well as acting as a solution for carrying precursors of the HA/CS link molecule versican/aggregan for the purpose of providing a supramolecular complex with link protein to form a strongly hydrated space filling gel of poly-anionic glycosaminoglycan chains covalently attached to the core and contributing to the strength of the bladder GAG layer.

N-acetyl D-glucosamine is also a derivative of glucose obtained by chemical hydrolysis of chitin. This polysaccharide is readily soluble in water and extremely bioavailable. N-acetyl D-glucosamine binds to glucuronic acid as well as galactose making it a precursor to hyaluronic acid, keratansulfate and chondroitin sulfate. This unique derivative aids a proteoglycan, collagen and glycosaminoglycan production. N-acetyl D-glucosamine has also been shown to aid in the healing of soft tissue injury.

The embodiments of the present invention are safe and non-toxic in the therapeutic amounts as set forth herein. Each embodiment provides a specific benefit in relation to the treatment and/or prevention to thereby alleviate, lessen or prevent at least one symptom of interstitial cystitis (IC) or a related urinary tract condition in man or in animals. Thus, it can be realized that certain of the compositions of this invention, e.g., those comprised of chondroitin sulfate, N-acetyl D-glucosamine and hyaluronic acid provide a unique combination for direct instillation into the bladder and/or for systemic use of replacement components and metabolic precursors which advantageously stimulate the production of glycosaminoglycans including hyaluronic acid, proteoglycans and collagen, thereby assisting the body's natural repair mechanisms and as a coating for the bladder epithelium and to inhibit certain inflammatory mediators by its direct effect on CD44 and TSG-6, and Lyve receptor sites.

Another important aspect of the compositions of the invention is that they are adapted for direct instillation into the bladder and are especially well suited for use as a "medical device" for physical lavage or flushing of the bladder as well as to provide a protective coating to the epethelium. The highly negative ionic charge and unique characteristics of the compositions set forth herein act to directly trap or bind positively charged particles present in the bladder, e.g., free radicals released from the inflammatory processes, and physically remove such particles from the epithelial surface of the bladder. Because of their capacity for multidimensional disposition, hydrophilic nature, prominent presence of negative charges and lubricating/coating capabilities, the compositions provided herein also exhibit selective permeability, and support for the damaged epithelium of the bladder of patient suffering from interstitial cystitis, which are essential characteristics to aid the return of the bladder wall (epithelium and interstitial matrix etc.) to homeostasis.

Thus, in one embodiment, the compositions of the invention have been specially adapted for intra-bladder instillation and/or parenteral (e.g., intravenous or intramuscular) are sterile solutions or suspensions comprised of therapeutic amounts of chondroitin sulfate and hyaluronan (hyaluronic acid). In addition to the afore-mentioned active agents, it can be appreciated by one of skill in the art that the compositions of the invention which are adapted for intra-bladder instillation and/or parenteral use can also comprise preservatives, pharmaceutically active carriers, excipients, stabilizers, buffers, antimicrobial growth inhibitors and the like and the use of such is contemplated by the invention.

It is contemplated by the invention that the compositions provided herein may be useful in methods for the direct intra-bladder instillation and/or parenteral (systemic) treatment and/or prevention of interstitial cystitis. In one embodiment the compositions of the invention are comprised of therapeutic amounts of chondroitin sulfate and hyaluronan (hyaluronic acid). It is presently preferable that the compositions of the invention are sterile solutions and/or are suspensions comprised of chondroitin sulfate and hyaluronan. In one preferred embodiment, the chondroitin sulfate and hyaluronic acid of the composition is in a solution of N-acetyl D-glucosamine.

However, it is contemplated that other formulations are possible and are within the scope of the invention, e.g., a powdered formulation suitable for reconstitution with a suitable injectable liquid or for addition to a preselected liquid suitable for instillation into the bladder, e.g., lactated ringers or normal saline solution. In particular, it can be appreciated by one of skill in the art that the active agents of the compositions can be stored in a freeze dried or lyophilized state for reconstitution and use at a desired time.

A presently preferred embodiment of the invention comprises a composition adapted for direct intra-bladder instillation and/or parenteral administration comprised of chondroitin sulfate and hyaluronan wherein the therapeutic amount of chondroitin sulfate is from between about 0.5 grams to about 1.5 grams of a suitable chondroitin sulfate per unit dose of the composition. In one embodiment, the therapeutic amount comprises about 1 gram of CS4 chondroitin sulfate, or about 1 gram of CS6 chondroitin sulfate or about 1 gram of a mixture of CS4 and CS6 chondroitin sulfate per unit dose. In another embodiment, the therapeutic amount of chondroitin sulfate is about 1 gram of chondroitin sulfate comprised of about 40% CS4 chondroitin sulfate and about 60% CS6 chondroitin sulfate. In another embodiment, the chondroitin sulfate may comprise a mixture of CS4 and CS6 chondroitin sulfate wherein the mixture can be from about 70% CS4 to about 30% CS4 and from about 30% CS6 to about 70% CS6.

Presently preferred therapeutic amounts of hyaluronan include from about 10 mg to about 50 mg of hyaluronan per unit dose of the composition. An especially preferred therapeutic amount of hyaluronan is from about 20 mg to about 40 mg of hyaluronall per unit dose of the composition.

It can be appreciated by one of skill in the art that the hyaluronan can be selected from among any of a number of commercially available sources such as commercially available Sodium Hyaluronate. Likewise there are numerous commercially available sources of N-acetyl D-glucosamine and Cliondroitin Sulfate that are available for use in the compositions set forth herein.

In certain embodiments of the invention the compositions may optionally include therapeutic amounts of N-acetyl D-glucosamine for the compositions of the invention that are from about 0.5 grams to about 1.5 grams of N-acetyl D-glucosamine per unit dose. An especially preferred therapeutic amount of N-acetyl D-glucosamine is about 1 gram of N-acetyl D-glucosamine per unit dose of the composition. In one embodiment, the CS and HA comprising the compositions of the invention are in about a 10% solution of N-acetyl D-glucosamine.

Another presently preferred embodiment of the invention provides a composition adapted for direct intra-bladder instillation and/or parenteral injection comprised of a sterile solution or suspension comprised of about 1 gram of chondroitin sulfate as a mixture of about 40% CS4 and 60% CS6 chondroitin sulfate; and about 20-40 mg but especially about 30 mg of hyaluronan (e.g, Na Hyaluronate) per unit dose of the composition. Still another einbodiment of the invention provides compositions for direct intra-bladder instillation and/or parenteral injection comprised of a 5 cc/unit dose wherein the composition compinses about 500 mg of a suitable chondroitin sulfate and about 25 mg of a suitable hyaluronic acid (e.g. about 500,000 KD HA) in a 10% solution of N-acetyl D-glucosamine. Yet another embodiment of the invention provides compositions for direct intra-bladder instillation and/or parenteral injection comprised of a 10 cc/unit dose wherein the composition comprises about 1000 mg of a suitable chondroitin sulfate and about 50 mg of a suitable hyaluronic acid (e.g about 500,000 KD HA) in a 10% solution of N-acetyl D-glucosamine.

One example of a preferred embodiment of the invention comprises a 10 ml unit dose of the composition. It can be appreciated that this unit dosage can be added to a suitable amount of a liquid selected for direct bladder instillation, e.g., including but not limited to water, lactated ringers, normal saline, and DMSO. It can also be appreciated that the methods of the invention for the treatment and/or prevention of interstitial cystitis can utilize more than one unit dose per treatment and/or the treatment regimen can vary depending upon the severity of the condition, age and health of the patient and the like.

In one embodiment of the invention, a unit dose of the composition can be made as follows. One gram of chondroitin sulfate powder is admixed into a 20% solution of N-acetyl D-glucosamine. The resulting solution is then admixed with 4 ml of a 10 mg/ml solution of sodium hyaluronate. The final concentration of chondroitin sulfate in the composition is 100 mg/ml and the final concentration of sodium hyaluronate in the composition is 0.5 mg/ml.

One presently preferred embodiment of the invention provides a composition adapted for direct intra-bladder instillation and/or parenteral administration which consists essentially of therapeutic amounts of chondroitin sulfate and hyaluronan.

In another embodiment the invention provides a composition adapted direct intra-bladder instillation and/or parenteral administration which comprises therapeutic amounts of chondroitin sulfate; and hyaluronan wherein the molecular weight per unit dose of the composition is from between about 450,000 Daltons to about 1,100,000 Daltons. In yet another embodiment the invention provides a composition adapted for direct intra-bladder instillation and/or parenteral administration which comprises therapeutic amounts of chondroitin sulfate; and hyaluronan wherein the molecular weight per unit dose of the composition is from between about 500,000 Daltons to about 1,000,000 Daltons. In yet another embodiment the invention provides a composition adapted direct intra-bladder instillation and/or parenteral administration which comprises therapeutic amounts of chondroitin sulfate and hyaluronan wherein the molecular weight per unit dose of the composition is from between about 550,000 Daltons to about 700,000 Daltons but is especially about 600,000 Daltons.

In a preferred embodiment the invention provides a composition adapted direct intra-bladder instillation and/or parenteral administration which comprises therapeutic amounts of chondroitin sulfate and hyaluronan wherein the molecular weight per unit dose of the composition is greater than about 450,000 Daltons. In another embodiment, the invention provides a composition adapted for direct intra-bladder instillation and/or parenteral administration which comprises therapeutic amounts of chondroitin sulfate and hyaluronan wherein the molecular weight per unit dose of the composition is greater than about 550,000 Daltons.

In yet another embodiment of the invention the compositions set forth herein can further comprise a therapeutic amount of a suitable antibiotic. Suitable antibiotics for use in the compositions provided herein include, but are not limited to any of the antibiotics that are known in the art for the treatment and/or prevention of bacterial cystitis. As can be appreciated by one of skill in the art, the choice of antibiotic and therapeutic amount can depend many factors including, but not limited to, e.g., the etiology of the infectious organism being treated or personal preference of the treating veterinarian or physician.

The compositions of the invention can also further comprise other therapeutic agents insofar as it is generally used as a therapeutic for interstitial cystitis. Examples of other such therapeutic agents include, but are not limited to, synthetic and non-synthetic corticosteroid agents, nonsteroidal anti-inflammatory drugs, antirheumatics, immmunoregulators, immunosuppressors, and interleukin production inhibitors. Specific examples of corticosteroid agents include, but are not limited to dexamethasone, hydrocortisone, triamcinolone, betamethasone, predonisolone, methylpredonisolone, halopredone, beclomethasone and the like.

Specific examples of non-steroidal anti-inflammatory agents include, but are not limited to diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, fliurbiprofen and the like.

In one embodiment, the compositions of present invention can further comprise of at least one pyrazolyl benzenesulfonamide compound, e.g., as set forth in U.S. Pat. Nos. 5,756,529 and 5,466,823, the contents of which is incorporated herein by reference. In particular, the compositions of the invention can further comprise a diaryl substituted pyrazole useful for treatment of inflammation and/or pain. It is specifically contemplated that the compositions of the invention can further comprise therapeutic amounts of any of the class of diaryl substituted pyrazoles their isomers, analogs and/or metabolites. In particular, these compounds reduce inflammation and/or pain primarily via inhibition of cyclooxygenase-2 (COX-2). In a preferred embodiment of the invention, the compositions provided further comprise a non-steroidal agent that reduces inflammation and/or pain primarily via inhibition of cyclooxygenase-2 (COX-2) and with the substantial absence of inhibition of cyclooxygenase-1 (COX-1). Examples of suitable diaryl substituted pyrazoles for use in the compositions of the invention, include but are not limited to celecoxib, rofecoxib and the like.

Examples of other agents which may be added to the core compositions set forth herein include, axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and the like.

In a particularly preferred embodiment, the invention also provides a composition adapted direct intra-bladder instillation comprised of therapeutic amounts of chondroitin sulfate; hyaluronan and a suitable antioxidant or free radical scavenger. In one embodiment, the compositions of the invention can further comprise a therapeutic amount of suitable superoxide dismutase (SOD) or other antioxidant including, but not limited to, examples set forth in U.S. Pat. No. 6,127,356 to Crapo et al., the contents of which are incorporated herein by reference.

In another embodiment, the invention provides a composition adapted for parenteral administration, that is useful for the treatment and/or prevention of interstitial cystitis, the composition comprising therapeutic amounts of: chondroitin sulfate and hyaluronan. In another embodiment, a related method of treatment and/or prevention of synovitis in an animal is provided which comprises parenterally administering a therapeutic amount of a composition comprised of chondioitin sulfate and hyaluronan to the animal. in particular, the invention provides the surprising discovery of a synergistic effect provided by the combination of the active agents of the compositions of the invention in the treatment of traumatic synovitis when the compositions are administered parenterally, e.g., intravenous administration.

The foregoing description of preferred embodiments of the invention have been presented for purposes of illustration and description. They are not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A composition formulated for direct bladder instillation and for treatment of interstitial cystitis or a related urinary tract condition in man or in animals consisting essentially of from about 0.5 grams to about 1.5 grams per unit dose of the composition of chondroitin sulfate and from about 10 mg to about 50 mg per unit dose of the composition of hyaluronan.

2. The composition of claim 1, wherein the suitable chondroitin sulfate is CS4 chondroitin sulfate.

3. The composition of claim 1, wherein the suitable chondroitin sulfate is CS6 chondroitin sulfate.

4. The composition of claim 1, wherein the suitable chondroitin sulfate is a mixture of CS4 chondroitin sulfate and CS6 chondroitin sulfate.

5. The composition of claim 1, wherein said composition is a sterile solution.

6. The composition of claim 1, wherein said composition is a sterile suspension.

7. A method for treatment of interstitial cystitis or a related urinary tract condition in man or in animals, comprising administering directly into the bladder of said man or animals in need thereof a therapeutic amount of the composition of consisting essentially of a therapeutic amount chondroitin sulfate and hyaluran.

8. The method of claim 7, wherein the composition is administered by direct parenteral instillation into the bladder.

9. The method of claim 7, wherein the composition comprises between about 0.5 grams to about 1.5 grams of a suitable chondroitin sulfate per unit dose of the composition.

10. The method of claim 9, wherein the suitable chondroitin sulfate is CS4 chondroitin sulfate.

11. The method of claim 9, wherein the suitable chondroitin sulfate is CS6 chondroitin sulfate.

12. The method of claim 9, wherein the suitable chondroitin sulfate is a mixture of CS4 chondroitin sulfate and CS6 chondroitin sulfate.

13. The method of claim 7, wherein the composition comprises about 10 mg to about 50 mg of hyaluronan per unit dose of the composition.

14. The method of claim 7, wherein the composition is a sterile solution.

15. The method of claim 7, wherein the composition is a sterile suspension.

* * * * *